United States Patent [19]

DeLuca et al.

[11] Patent Number: 4,940,700

[45] Date of Patent: Jul. 10, 1990

[54] SECO-STEROL COMPOUNDS EFFECTIVE IN INDUCING CELL DIFFERENTIATION

[75] Inventors: Hector F. DeLuca; Heinrich K. Schnoes; Wan F. Lau, all of Madison, Wis.

[73] Assignee: Wisconsin Alumni Research Foundation, Madison, Wis.

[21] Appl. No.: 367,126

[22] Filed: Apr. 30, 1987

Related U.S. Application Data

[63] Continuation of Ser. No. 726,496, Apr. 23, 1985, abandoned.

[51] Int. Cl.$^5$ .......................... A61K 31/59; C07J 9/00; C07J 1/00
[52] U.S. Cl. ................................ 514/167; 260/397.2; 260/397.5
[58] Field of Search .......................... 260/397.2, 397.5; 514/167

[56] References Cited

U.S. PATENT DOCUMENTS 4,800,198  1/1989  DeLuca et al. .................... 514/167

OTHER PUBLICATIONS

Chemical Abstracts, vol. 108 (1988), #180270T, DeLuca et al.
Chemical Abstracts, vol. 107 (1987), #191,147 P, Ostrem et al.
Chemical Abstracts, vol. 106 (1987), #131710M, DeLuca et al.
Frampton et al, "Cancer Research", Sep. 1983, pp. 4443–4447.

*Primary Examiner*—Joseph A. Lipovsky
*Attorney, Agent, or Firm*—Andrus, Sceales, Starke & Sawall

[57] ABSTRACT

The invention provides new seco-sterol compounds which are effective in inducing the differentiation of malignant cells and are therefore useful for the treatment of malignancies such as leukemia.

12 Claims, No Drawings

SECO-STEROL COMPOUNDS EFFECTIVE IN INDUCING CELL DIFFERENTIATION

This invention was made in the course of research supported by the U.S. Government under a grant from the Public Health Service. The Government has certain rights to this invention.

This application is a continuation of application Ser. No. 726,496, filed Apr. 23, 1985, now abandoned.

TECHNICAL FIELD

This invention relates to a novel group of compounds that are effective in inducing the differentiation of malignant cells. More specifically, this invention relates to the preparation of a group of seco-sterol compounds which find use for the treatment of malignancies such as leukemia.

BACKGROUND

A useful therapeutic method for the treatment of malignancies is the administration of compounds that stimulate the differentiation of malignant cells to normal cells, thereby inhibiting and/or reversing the malignant transformation. Thus, it has been shown by Suda et al. (U.S. Pat. No. 4,391,802) that 1α-hydroxyvitamin D compounds (e.g. specifically 1α,25-dihydroxyvitamin $D_3$ and 1α-hydroxyvitamin $D_3$) possess, for example, potent antileukemic activity by virtue of inducing the differentiation of malignant cells (specifically leukemia cells) to non-malignant macrophages (monocytes). Hence, these compounds are useful for the treatment of certain malignancies, specifically for the treatment of leukemia (Suda et al., U.S. Pat. No. 4,391,802). When used for such treatment, however, these known 1α-hydroxyvitamin D compounds have the disadvantage that they are also very potent calcemic agents, i.e. they cause elevated blood calcium levels by stimulating intestinal calcium absorption and bone calcium resorption. This calcemic activity represents, indeed, the well-known, classical function of these compounds. Furthermore, the cell differentiation activity (and, hence, antileukemic activity) of these compounds correlates with their calcemic activity. For example, 1,25-dihydroxyvitamim $D_3$, the most potent compound in inducing the differentiation of malignant cells to macrophages, is also the most potent vitamin D metabolite in stimulating calcium transport or raising serum calcium levels. For practical use as cell-differentiating agents, this potent calcemic activity is, of course, an undesired side effect, since the doses required for efficacy in differentiating malignant cells can lead to excessively high and non-physiological serum calcium levels in the treated subjects.

DISCLOSURE OF INVENTION

A novel class of secosterol compounds has now been prepared which exhibit high differentiation activity towards malignant cells, such as leukemia cells, but do not have the undesired side-effects (potent calcemic action) of some of the known compounds mentioned above. This selectivity and specificity of action makes the secosterols of this invention useful and preferred agents for the treatment of malignancies such as leukemia.

This class of secosterols is characterized by the general structures I and II shown below:

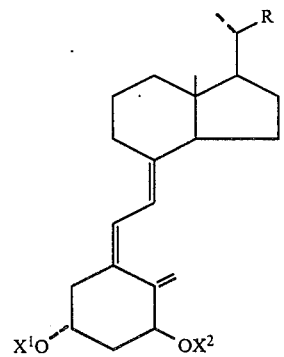

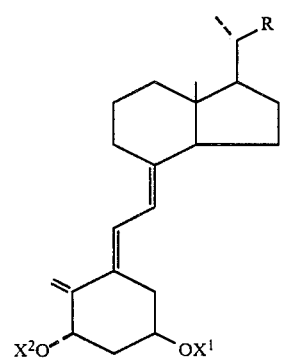

where R is methyl, ethyl or propyl and where each of $X^1$ and $X^2$ represent, independently, hydrogen or an acyl group.

As used in this description and the claims, an acyl group is an alkanoyl group of 1 to 6 carbons in all its isomeric forms, or an aroyl group, such as benzoyl, or halo-, nitro- or alkyl-substituted benzoyl groups, or a dicarboxylic acyl group such as oxalyl, malonyl, succinoyl, glutaroyl, or adipoyl. An alkyl group is a hydrocarbon radical of 1 to 6 carbons in all isomeric forms.

Purely structurally, this class of secosterols has similarity with some of the known vitamin D compounds. Unlike the known vitamin D compounds, however, the secosterols of the present invention do not express the classic vitamin D activities in vivo, i.e. stimulation of intestinal calcium transport, or the mobilization of bone calcium, and hence they cannot be classified as vitamin D derivatives from the functional point of view. In light of the prior art, it was all the more surprising and unexpected then, to find that these secosterols are remarkably effective in inducing the differentiation of leukemia cells to normal (non-malignant) macrophages, since, as mentioned above, potent cell differentiation activity among the known vitamin D-related compounds was always closely correlated with potent calcemic activity. Thus, the secosterols of the present invention overcome the shortcomings of the known vitamin D-related antileukemic agents mentioned above, and can be considered preferred agents for the control and treatment of malignant diseases such as leukemia. This finding provides an effective method for the treatment of malignancies, since the above described secosterols can be administered to subjects in doses sufficient to cause differentiation of malignant cells to normal cells, without producing simultaneously unphysiologically high and deleterious blood calcium levels.

Biological Properties of Secosterol Compounds

Biological activity of compounds of structure I in the differentiation of human leukemia cells.

Chemicals and reagents required for the assays below were obtained from commercial sources as follows: 4β-phorbol 12-myristate-13-acetate (PMA), Nitro blue tetrazolium (NBT) and reagents for α-napthyl acetate esterase assay (α-naphthyl acetate, TRIZMAL ™ 7.6 buffer concentrate, Mayer's hematoxylin solution, Fast Blue RR salt, citrate concentrate, ethylene glycol monomethyl ether) were obtained from Sigma Chemical Company, St. Louis, MO; sheep erythrocytes (50% cells in Alsevers solution), fetal calf serum and RPM1-1640 medium were from Gibco Laboratories, Grand Island, N.Y., and rabbit antiserum to sheep erythrocytes (rabbit hemolysin) was from Flow Laboratories, McLean, Va.

Cell culture:

10 ml aliquots of human leukemia cells (HL-60 cells) ($\sim 2 \times 10^5$ cells/ml in RPM1-1640 media with 10% heat-inactivated fetal calf serum) were plated out on Petri dishes and cultured at 37° C. in a 5% $CO_2$ atmosphere. After 16 hours, duplicate dishes were dosed with various amounts of test compounds (as listed in Table 1, below) dissolved in 10–20 μl of ethanol. control cultures received ethanol alone. The cells were harvested 4 days after dosing and an aliquot of each was counted under a hemocytometer. To assess the degree of differentiation induced by the test compounds, the harvested cultures were resuspended in phosphate-buffered saline (PBS) ($\sim 10^6$ cells/ml) and each of the following three assays were then performed on aliquots of the cell cultures.

(a) Nitro blue tetrazolium (NBT) reduction assay for differentiation.

This assay is based on the fact that monocytes can be induced by phorbol esters to produce superoxide. The superoxide can be detected by its capability to reduce soluble (nitro-blue tetrazolium (NBT) to a black:blue precipitate, formazan. The NBT-reduction activity exhibited by the HL-60 cells thus provides a measure of their differentiation to non-malignant monocytes. The assay was performed according to the procedure given by Yen et al., J. Cellular Physiol. 118, 277 (1984). The NBT reagent was prepared by dissolving 50 mg NBT and 5 μg of 4β-phorbol 12 myristate-13-acetate in 50 ml of phosphate-buffered saline. This reagent (200 μl) was added to 200 μl of the harvested cells (ca. $10^6$ cells/ml phosphate-buffered saline). The mixture was incubated in a water bath at 37° C. for 30 min. The cells were then counted and the percentage of cells that reduced NBT to formazan blue was recorded. Results are given in Table 1, below.

(b) Assay for rosette formation.

This assay is based on rosette formation between differentiated monocytes and sheep erythrocytes coated with rabbit antibody and mouse complement. The assay was done according to the procedure of Lotem and Sachs, Internat. J. Cancer 15, 731 (1975). Sheep erythrocytes were washed three times with posphate-buffered saline and resuspended to a 0.5% (v/v) suspension. Equal volumes of erythrocytes and a 1:1500 dilution of rabbit antiserum to sheep erythrocytes were mixed and incubated at 37° C. for 30 min. The antibody-coated erythrocytes (EA) were washed three times with posphate-buffered saline, pH 7.0 and resuspended at 0.5% (v/v). Fresh mouse blood was spun down and the serum was collected. Equal volumes of EA and a 1:10 dilution of the mouse serum were mixed and incubated at 37° C. for 30 min, then washed three times with phosphate-buffered saline and resuspended in RPMI medium, 1% (v/v) to give the erythrocytes coated with antibody and complement (EAC), 100 μl of EAC was mixed with an aliquot of HL-60 cells (about $10^6$ cells in 100 μl RPMI), incubated for 30 min at 37° C., and then centrifuged for 3 min at 500 xg. The pellet was dispersed and the cells with attached EAC (i.e. the number of rosetts) were determined, and expressed as a percent of the total cells present. The "% rosette formation", indicative of the differentiation of HL-60 cells to monocytes, is listed in Table 1, below.

(c) Assay for α-naphthyl acetate esterase activity.

α-Naphthyl acetate esterase is an enzyme characteristic of monocytes. The presence of the enzyme thus indicates differentiation of HL-60 cells to monocytes. The assay is based on the enzymatic hydrolysis of the α-naphthyl acetate to liberate free naphthol which couples with a diazonium salt to form highly colored deposits at the sites of enzyme activity. The assay was carried out as described in Technical Bulletin No. 90 (Sigma Chemical Co., St. Louis, Mo. 63178). Cells were fixed on slides in a citrate-acetone-methanol fixative for 30 sec at room temperature. The slides were then washed with deionized water and air-dried at least 20 min. The slides were then stained in a staining solution prepared by dissolving 25 mg Fast Blue RR salt in 50 ml of a 1:10 dilution of TRIZMAL ™ buffer concentrate pH 7.6, followed by the addition of 20 mg of α-naphthyl acetate (in 2 ml ethylene glycol monomethyl ether). The slides were incubated at 37° C. for 30 min (protected from light). They were then washed, counter-stained for 5–10 min in Mayer's hematoxylin solution, washed and then air-dried. The percentage of cells with black granulation, indicative of α-naphthyl esterase activity, was determined. Results are listed in Table 1, below.

TABLE 1

Percent differentiation of HL-60 cells induced by seco-sterols or by known 1α-hydroxyvitamin D compounds administered at various concentrations as measured by NBT-reduction, rosette formation and esterase activity assays

| Compound Administered | Concentration (M) | NBT Reduction (%) | Rosette Formation (%) | Esterase Activity (%) |
|---|---|---|---|---|
| EtOH | Control | 4.5 | 9 | 3.5 |
| Secosterol I (R = $CH_3$, $X^1 = X^2 = H$) | $1 \times 10^{-7}$ | 9 | 9 | 2 |
|  | $1 \times 10^{-6}$ | 14 | 23 | 11 |
|  | $5 \times 10^{-6}$ | 59 | 68 | 69 |
| Secosterol I (R = $CH_2CH_3$, $X^1 = X^2 = H$) | $1 \times 10^{-7}$ | 15 | 23 | 30 |
|  | $1 \times 10^{-6}$ | 28 | 30 | 77 |
|  | $1 \times 10^{-5}$ | 69 | 70 | 91 |
| 1α-OH-$D_3$ | $1 \times 10^{-7}$ | 10 | 44 | 12 |
|  | $1 \times 10^{-6}$ | 39 | 61 | 90 |
|  | $1 \times 10^{-5}$ | 85 | 79 | 100 |
| 1α,25-$(OH)_2D_3$ | $1 \times 10^{-8}$ | 39 | 44 | 65 |
|  | $1 \times 10^{-7}$ | 83 | 76 | 90 |

The above results illustrate the efficacy of the seco-sterols of general structure I as agents for the differentiation of human leukemia cells to macrophages (monocytes). The compounds show highly significant activity in all three of the differentiation assays used; 50% differentiation is achieved at concentrations of about $10^{-6}$ M.

For comparative purposes, the table above also includes the cell differentiation activity exhibited by 1α-hydroxyvitamin $D_3$ (1α-OH-$D_3$) and 1α,25-dihydroxyvitamin $D_3$ (1,25-$(OH)_2D_3$), two known vitamin D derivatives with potent antileukemic action. The tabulated data show that the level of activity of the seco sterols (I) is lower than that shown by 1,25-$(OH)_2D_3$ (the most potent vitamin D-derived agent for differentiation of leukemia cells), but is approximately equivalent to that shown by 1α-hydroxyvitamin $D_3$, a compound known to be effective in the treatment of human leukemoid diseases (Suda et al., U.S. Pat. No. 4,391,802).

Assay of secosterols of structure I for bone calcium mobilization and calcium transport.

Male weanling rats, purchased from the Holtzman Co., Madison, Wis., were fed the low calcium, vitamin D-dificient diet described by Suda et al. [J. Nutr. 100, 1049 (1970)] ad libitum for 3 weeks. The rats were then divided into 4 groups of 6 animals each. The first group (control group) received 0.05 ml of 95% EtOH by intrajugular injection. The second and third groups were dosed by the same route with 625 picomoles and 6250 picomoles, respectively, of secosterol I (R=$CH_3$, $X^1$=$X^2$=H) dissolved in 0.05 ml of EtOH, and the fourth group received an intrajugular injection of 625 picomole of 1α,25-dihydroxyvitamin $D_3$ (in 0.05 ml of EtOH). Seven hours after dosing, the rats were killed by decapitation and their blood was collected and centrifuged to obtain serum. Serum calcium concentration was determined with an atomic absorption spectrometer according to the conventional protocol. Results are listed in Table 2 below.

The small intestines of these same rats were removed, rinsed and everted for measurement of calcium transport activity according to the technique of Martin and DeLuca [Am. J. Physiol. 216, 1351 (1969)]. The measured intestinal calcium transport activity data, expressed as the ratio of serosal/mucosal calcium concentration, are also listed in Table 2.

TABLE 2

| Compound Administered | Amount (pmole) | Serum Calcium Concentration (mg/100 ml) mean ± S.D. | Intestinal Ca-transport [Ca-serosal]/ [Ca-mucosal] mean ± S.D. |
|---|---|---|---|
| EtOH (control) | — | 2.6 ± 0.1 | 3.6 ± 0.1 |
| Secosterol I (R = $CH_3$, $X^1$ = $X^2$ = H) | 625 | 2.9 ± 0.1 | 3.4 ± 0.1 |
| Secosterol I (R = $CH_3$, $X^1$ = $X^2$ = H) | 6250 | 3.0 ± 0.1 | 3.4 ± 0.1 |
| 1,25-$(OH)_2D_3$ | 625 | 3.8 ± 0.2 | 6.7 ± 0.8 |

The above results show that secosterol I (R=$CH_3$, $X^1$=$X^2$=H) expresses no significant calcemic activity even at high doses. The compound does not elevate serum calcium levels and thus is devoid of significant bone calcium mobilization activity. Further, the compound does not stimulate calcium transport in the intestine at a dose level of 6250 picomole per animal. Under the same conditions, the known active vitamin D metabolite, 1,25-$(OH)_2D_3$, is, as expected, fully active at 10 times lower dose levels.

It can be concluded, therefore, that these seco steroids of general structure I (where R is hydrogen, methyl, ethyl, propyl) do not carry out the classical vitamin D functions in vivo, since they elicit no significant in vivo biological response with respect to bone mineral mobilization, and intestinal calcium transport activation.

The above data establish that the seco-sterols of this invention possess an unusual and unexpected spectrum of activities. They exhibit highly significant cell differentiation activity, like some of the known vitamin D-related compounds, but do not express the calcemic activity typical of vitamin D-derivatives. Thus, in being devoid of the undesired calcemic action of the known antileukemic vitamin D-compounds, the seco-steroids of this invention provide a novel and preferred method for the treatment of malignancies, such as leukemia.

The compounds may be formulated as pills, capsules or tablets, or in liquid form as solutions, emulsions, dispersions or suspensions in pharmaceutically innocuous and acceptable solvent or oils, and such preparations may contain in addition other pharmaceutically innocuous or beneficial components, such as antioxidants, emulsifiers, coloring agents, binders or coating materials.

The compounds may be administered as oral doses, or by injection or infusion of suitable sterile solutions. The compounds are advantageously administered in amounts sufficient to effect the differentiation of malignant cells to normal macrophages. Dosages from 2 μg to 1000 μg per day are suitable, it being understood that the amounts given are to be adjusted in accordance with the severity of the disease, and the condition and response of the subject as is well understood in the art.

Preparation of seco-sterol compounds.

The secosterol of structure I or II shown above are new compounds. A related substance, 1α-hydroxypregnacalciferol, has been prepared by Lam et al. [Steroids 26, 422 (1975)]. The secosterols of structures I and II, where R is methyl, ethyl or propyl, can be prepared according to the general process illustrated in Process Scheme I. Suitable starting materials are the i-ether steroids of general structure 1, where, depending on the final product desired, R may be methyl, ethyl or propyl. Conversion of a compounds of structure 1 to the 5-ene steroid of structure 2 is accomplished by solvolysis in glacial acetic acid, according to known procedures. The 5-ene steroid is then dehydrogenated to the 5,7-diene steroid (3) using the sequence of allylic bromination at C-7 followed by dehydrobromination, and the acetate group of compound 3 is saponified to obtain the corresponding alcohol of structure 4. Irradiation of a solution of alcohol 4 with ultraviolet light open ring B of the steroid to provide the initial secosterol derivative (the 5(10),6,8-triene), which can be purified and isolated if desired by standard chromatographic methods, but can also, and generally most advantageously, be directly thermally isomerized to the 5,7,10(19)-triene compounds of structure 5.

The further conversion of this intermediate to the desired 1α-hydroxylated analog can be accomplished according to the general procedures given in U.S. Pat. Nos. 4,195,027 and 4,260,549. Intermediate 5 (Process Scheme I) is first tosylated to obtain the 3β-tosylate (6), and this tosylate is then solvolyzed in buffered methanol to produce the 6-methoxy-3,5-cyclo-derivative represented by structure 7. Solvolysis of the tosylate in other alcoholic solvents (e.g. ethanol, propanol, butanol, etc.) produces the analogous 6-0-alkyl-3,5-cyclo intermedites, where the alkyl group derives from the alkyl portion (e.g. ethyl, propyl, butyl, etc.) of the alcohol used. Any of these 6-0-alkyl-homologs of compound 7 can be used for the subsequent reactions of this process. Oxidation of intermediate 7 with selenium dioxide in the presence of a hydroperoxide introduces the desired 1α-hydroxy function and provides compound 8. This intermediate is then solvolyzed in a medium containing a low-molecular weight orgnaic acid to yield the 3-acylate, having structure 9 ($X^1$=acyl, $X^2$=H) and the corresponding 5,6-trans-isomer of structure 10 ($X^1$=acyl, $X^2$=H) (where the acylate groups in each case derive from the organic acid used in the solvolysis reaction). These 5,6-cis and 5,6-trans 3β-acylates (compounds 9 and 10) are advantageously separated at this stage so as to obtain each compound in pure form. They can then be subjected to saponification (e.g. base in methanol) to obtain the corresponding free hydroxy compounds 9 ($X^1$=$X^2$=H) and 10 ($X^1$=$X^2$=H). Alternatively, the monoacylates of 9 and 10, or the free hydroxy compounds can be subjected to acylation under conventional and known conditions (e.g. acid anhydride or acyl halide in a nitrogenous base solvent) to produce any desired C-1-mono acyl, C-3-mono acyl or C-1,3-diacyl derivative, e.g. the compounds of structure 9 or 10, where $X^1$=acyl and $X^2$=H, or where $X^1$=H and $X^2$=acyl, or where $X^1$=acyl and $X^2$=acyl, where the acyl groups may be the same or different.

It is evident from the above description and the Process Scheme that the nature of the side-chain in the starting material determines the side-chain structure in the final products. Thus, using as starting material the sterol of structure 1, where R is methyl, provides the products of structures 9a and 10a, where R is methyl. Compound 1, where R is ethyl, as starting material, gives products 9a and 10a, where R is ethyl, and upon processing of steroid 1, where R is propyl, through the above described process, there is obtained the product 9c and 10c, where R represents propyl.

The 5,6-trans-compounds of structure 10 in Process Scheme I have utility as biologically active analogs of the corresponding 5,6-cis-compounds of structure 9, or they may be converted to the 5,6-cis products of structure 9, by the trans to cis isomerization processes well-known in the art.

Preparation of starting materials.

The starting materials of structure 1 (where R=CH₃, CH₂CH₃ or CH₂CH₃CH₃) can be prepared by conventional methods from stigmasterol. Thus, by conversion of stigmasterol of its i-ether derivative, followed by ozonolytic cleavage of the side-chain double bond, and subsequent hydride reduction, there is obtained the known 22-alcohol, having the structure:

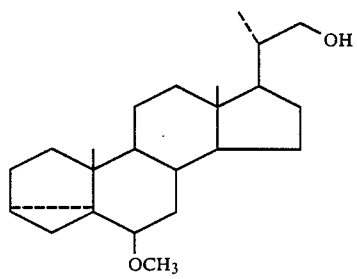

Tosylation of this alcohol, followed by hydride reduction of this 22-tosylate provides directly the compound of structure 1, where R=CH₃.

Treatment of the above 22-tosyl intermediate with sodium cyanide gives the corresponding 23-nitrile derivative. By two-step hydride reduction of this nitrile, there is obtained the 23-alcohol which, after tosylation, and another hydride reduction of this 23-tosyloxy intermediate, provides the starting compound of structure 1, where R=ethyl.

Similarly, the above 23-tosyloxy intermediate, by treatment with sodium cyanide, gives the corresponding 24-nitrile derivative, which after hydride reduction (to obtain the 24-alcohol) and another tosylation and hydride reduction sequence, provides the compound of structure 1, where R represent n-propyl.

The preparation of the novel compounds of this invention is more specifically described by the following examples. In these examples, the identification of products by Arabic numerals (e.g. compounds 1, 2, 3, etc.) refers to the structures so numbered in the Process Scheme.

EXAMPLE 1

Preparation of Compounds 9a and 10a ($X^1$=$X^2$=H) 3β-acetoxy-23,24-dinorchol-5-ene (2)

A solution of compound 1 (R=CH₃) (1.26 g, 3.8 mmol) in glacial acetic acid (35 mL) was heated at 70° C. for 4.5 h. The reaction mixture was cooled and poured into ice water, neutralized with 10% aqueous sodium hydroxide and extracted with chloroform (3×100 mL); the chloroform extracts were washed with water (2×50 mL), saturated sodium chloride solution (2×50 mL), dried over anhydrous magnesium sulfate, filtered and concentrated to dryness to give 0.86 g (63% yield) of compound 2 (R=CH₃).

Mass spectrum: m/e (relative intensity), 358 (M⁺, 2), 298 (100), 283 (15), 255 (6), 190 (9), 177 (23); ¹H-NMR (CDCl₃) δ0.66 (s, 18-H), 0.81 (d, J=7 Hz, 22-H), 0.95 (d, J=7.0 Hz, 21-H), 1.02 (s, 19-H), 2.06 (s, 3-OCOCH₃), 4.59 (m, 3-H), 5.38 (m, 6-H).

3β-acetoxy-23,24-dinorchola-5,7-diene (3) (R=CH₃)

A stirred solution of 2 (R=CH₃) (0.6 g, 8 mmol) in dry hexane (50 mL) containing finely divided sodium bicarbonate (0.7 g, 8 mmol) was heated to 80° C. at reflux under nitrogen before 1,3-dibromo-5,5-dimethylhydantoin (0.24 g, 0.85 mmol) was added. The reaction was allowed to proceed for 20 min. The mixture was cooled, then filtered and concentrated under reduced pressure.

The residue was immediately dissolved in 15 mL dry xylene and added dropwise to a mixture of xylene (25 mL) and s-collidine (0.4 g, 3.3 mmol). The mixture was flushed with nitrogen and was then cooled, diluted with benzene (50 mL), washed with 3% aqueous hydrochloric acid (3×20 mL), saturated sodium bicarbonate solution (1×25 mL), water (1×25 mL), saturated aqueous sodium chloride (2×25 mL), dried over anhydrous magnesium sulfate and filtered. The solvent was evaporated under reduced pressure.

The oily residue was dissolved in dry dioxane (40 mL) and p-toluenesulfonic acid (0.076 g, 0.4 mmol) was added. The mixture was flushed with nitrogen and refluxed at 70° C. for 0.5 h. After cooling, it was diluted with water (100 mL) and extracted with ethyl acetate (1×70 mL, 2×60 mL), the organic extract was washed with saturated sodium bicarbonate solution (1×30 mL), saturated sodium chloride (2×30 mL), dried over anhydrous magnesium sulfate, filtered and the solvent was evaporated under reduced pressure to give an oil containing the desired the 5,7-diene (3) (Rf 0.29 in 10% ethyl acetate-hexane) and the 2,4,6-triene (Rf 0.5 in 10% ethyl acetate:hexane). Preparative TLC using 10% ethyl acetate-hexane gave 0.26 g of 3 (R=CH$_3$) in ca. 43% yield.

UV (C$_2$H$_5$OH) $\lambda_{max}$ 282, 293, 272, 262 nm; mass spectrum: m/e (relative intensity), 356 (M$^+$, 5), 296 (100), 281 (59), 253 (56), 211 (29), 158 (75), 143 (74); $^1$H-NMR (CDCl$_3$): 0.62 (s, 18-H), 0.88 (d, J=7.0 Hz, 22-H), 0.95 (s, 19-H), 0.96 (d, J=7.0 Hz, 21-H), 2.04 (s, 3-OCOCH$_3$), 4.7 (m, 3-H), 5.4 (m, 7-H), 5.58 (m, 6-H).

3β-Hydroxy-23,24-dinorchola-5,7-diene (4) (R=CH$_3$)

A 10% sodium hydroxide in methanol solution was added dropwise to a stirred solution of 3 (R=CH$_3$) 259 mg; Rf 0.56 on 25% ethyl acetate-hexane) in ether (15 mL) over a 5 min period under nitrogen. The reaction proceeded at 23° C. and was monitored on TLC. It was completed within 35 min. The mixture was diluted with ether (100 mL) and water (30 mL) was added. The layers were separated and the aqueous layer was extracted with ether (2×50 mL). The combined ether fractions were washed with water (2×30 mL), saturated sodium chloride solution (2×30 mL), dried over anhydrous magnesium sulfate, filtered and evaporated to dryness under reduced pressure to give 200 mg of 4 (77% yield) after preparative TLC using 25% ethyl acetate/hexane.

(UV (EtOH): $\lambda_{max}$ 282, 293, 272, 262 nm; mass spectrum: m/e (relative intensity), 314 (M$^+$, 85), 296 (12), 281 (100), 261 (6), 255 (60), 211 (22), 171 (30), 143 (78); $^1$H-NMR (CDCl$_3$): δ0.62 (s, 18-H), 0.87 (d, J=7.0 Hz, 22), 0.95 (s, 19-H), 0.97 (d, J=7.0 Hz, 21-H), 3.63 (sh, 3-H), 5.38 (m, 7-H), 5.58 (m, 6-H).

Seco-sterol 5 (R=CH$_3$)

The 5,7-diene (4) (36 mg) dissolved in a mixture (1:4) of benzene-ether (100 mL) was placed in a jacket around a double-walled, water-cooled quartz immersion well equipped with a Hanovia 608A quartz-medium pressure mercury vapor ultraviolet lamp with a vycor filter. The mixture was irradiated for 4.5 min. The system was purged continuously with nitrogen throughout irradiation. The solvent was then removed under reduced pressure and the residue redissolved in dry ethanol. It was flushed with nitrogen and then heated to 70° C. at reflux under nitrogen for 3 h. It was then cooled and concentrated under reduced pressure. Purification by TLC using 20% ethyl acetate-hexane afforded 5 (R=CH$_3$) in 31.7% yield (11.4 mg).

UV (EtOH) $\lambda_{max}$ 264 nm; mass spectrum: m/e (relative intensity) 314 (M$^+$, 14), 296 (21), 281 (4), 271 (2), 253 (3), 136 (82), 118 (100); $^1$H-NMR (CDCl$_3$): δ0.54 (s, 18-H), 0.85 (d, J=7.0 Hz, 22-H), 0.94 (d, J=7.0 Hz, 21-H), 3.93 (m, 3-H), 4.82 (m sharp), 19(Z)-H), 5.04 (m (sharp), 19(E)-H), 6.02 (d, J=12.0 Hz, 7-H), 6.22 (d, J=12.0 Hz, 6-H).

Tosylate 6 (R=CH$_3$)

A solution of 5 (15 mg, 47 mmol, Rf 0.28 in 30% ethyl acetate-hexane) in dry pyridine (0.5 mL) was treated with p-toluenesulfonyl chloride (22 mg, 117 mmol) at 5° C. under nitrogen for 24 h. The reaction was quenched with ice water and the mixture extracted with ether (3×30 mL). The combined extracts were washed with 3% aqueous hydrochloric acid (2×30 mL), saturated aqueous sodium bicarbonate (1×50 mL), saturated sodium chloride solution (1×50 mL), dried over anhydrous magnesium sulfate and concentrated under reduced pressure to give 20 mg of tosylate 6 (R=CH$_3$) (Rf 0.6 in 30% ethyl acetate-hexane).

3,5-Cyclo-derivative 7 (R=CH$_3$)

The crude tosylate 6 (R=CH$_3$) (20 mg, 0.41 mmol, Rf 0.5 in 25% ethyl acetate-hexane) was added to a stirred solution of finely divided sodium bicarbonate (200 mg, 2.4 mmol) in anhydrous methanol (20 mL). The mixture was heated to 55° C. at reflux under nitrogen for 8 h, cooled, diluted with ether (100 mL) and washed with water (3×30 mL), saturated aqueous sodium chloride solution (1×30 mL), dried over anhydrous magnesium sulfate, filtered and the solvent was evaporated under reduced pressure. The crude mixture was chromatographed on preparative TLC using 10% ethyl acetate-hexane to obtain 7 (R=CH$_3$) (7 mg, Rf 0.66 in 10% ethyl acetate-hexane) in 50% yield.

Mass spectrum: m/e (relative intensity), 328 (M$^+$, 14), 296 (15), 281 (7), 253 (37), 159 (28), 135 (34), 145 (30); $^1$H-NMR (CDCl$_3$): δ0.55 (s, 18-H), 0.85 (d, J=7.0 Hz, 22-H), 0.93 (d, J=7.0 Hz, 21-H), 3.26 (s, 6(R)-OCH$_3$), 4.18 (d, J=10 Hz, 6-H), 4.89 (m (sharp), 19(Z)-H), 5.0 (d, J=10 Hz, 7-H), 5.06 (m sharp)

1α-Hydroxy-compound 8 (R=CH$_3$)

t-Butyl hydroperoxide (7 µl, 0.05 mmol) was added to a suspension of selenium dioxide (SeO$_2$; 1.1 mg, 10 µmole) in 1% dry pyridine-methylene chloride (5 mL) under nitrogen. The mixture was stirred at 23° C. for 0.5 h, then diluted with another 10 mL of 1% pyridine-methylene chloride solution. The mixture was cooled on an ice bath and intermediate 7 (R=CH$_3$) (7 mg, 21 µmole; Rf 0.62 in 25% acetate-hexane) in dry methylene chloride was introduced. The reaction was monitored on TLC. It proceeded at 23° C. for 16 min before 10% sodium hydroxide solution (20 mL) was added to quench the reaction. The mixture was diluted with ether (100 mL), phases were separated and the ether phase was washed with 10% aqueous sodium hydroxide (2×25 mL), water (2×20 mL), saturated aqueous sodium chloride (2×20 mL) and dried over anhydrous magnesium sulfate. It was filtered and the solvent was evaporated under reduced pressure. Preparative TLC of the residue using 25% ethyl acetate-hexane gave the 1α-hydroxy-derivative 8 (R=CH$_3$) (3 mg, Rf 0.15 in 25% ethyl acetate-hexane) in 41% yield.

Mass spectrum: m/e (relative intensity): 344 (M$^+$, 34), 312 (77), 271 (42), 177 (567), 135 (100), $^1$H-NMR (CDCl$_3$): δ0.55 (s, 18-H), 0.85 (d, J=7.0 Hz, 22-H), 0.94 (d, J=7.0 Hz, 21-H), 3.26 (s, 6(R)-OCH$_3$), 4.17 (m (sharp), 6-H), 4.22 (m (sharp), 1-H), 4.94 (d, J=9 Hz, 7-H), 5.16 (d, J=2.2 Hz, 19(Z)-H), 5.24 (d, J=2.2 Hz, 19(E)-H).

5,6-cis and trans secosterol 3β-acetates 9a and 10a (X$^1$=Ac, X$^2$=H)

A solution of 8 (R=CH$_3$) (3 mg) in glacial acetic acid (0.5 mL) was heated to 55° C. under nitrogen for 20 min, cooled and poured over ice cold sodium bicarbonate solution (15 mL) and extracted with ether (3×30 mL). The combined ether extracts were washed with saturated aqueous sodium bicarbonate (1×20 mL), water (2×20 mL), saturated sodium chloride (1×20 mL) and dried over anhydrous magnesium sulfate, filtered and concentrated under reduced pressure. The residue was chromatographed in 35% ethyl acetate-hexane (multiple elutions, 4 times) to yield 0.8 mg of the 5,6-cis-3β-acetate (9a) and 0.45 mg of the 5,6-trans-3β-acetate (10b), respectively.

Acetate 9a (X$^1$=Ac, X$^2$=H): UV (EtOH): λ$_{max}$ 264 nm, λ$_{min}$ 228 nm.; mass spectrum: m/e (relative intensity) 372 (M$^+$, 7), 312 (40), 269 (10), 189 (15), 134 (100); $^1$H-NMR (CDCl$_3$): δ0.54 (s, 18-H), 0.85 (d, J=7.0 Hz, 22-H), 0.92 (d, J=7.0 Hz, 21-H), 2.02 (s, 3-OCOCH$_3$), 4.4 (broad, 1-H), 5.01 (m (sharp), 19(Z)-H), 5.21 (m, 3-H), 5.33 (m (sharp), 19(E)-H), 6.0 (d, J=12.0 Hz, 7-H), 6.34 (d, J=12.0 Hz, 6-H).

Acetate 10a (X$^1$=Ac, X$^2$=H): UV (EtOH): λ$_{max}$ 273 nm, λ$_{min}$ 228 nm; mass spectrum: m/e (relative intensity) 372 (M$^+$, 3), 328 (4), 312 (14), 269 (6), 177 (37), 149 (58), 135 (100); $^1$H-NMR (CDCl$_3$): δ0.54 (s, 18-H), 0.85 (d, J=7.0 Hz, 22-H), 0.92 (d, J=7.0 Hz, 21-H), 2.02 (s, 3-OCOCH$_3$), 4.4 (broad, 1-H), 4.99 (m (sharp), 19(Z)-H), 5.13 (m (sharp), 19(E)-H), 5.8 (d, J=12.0 Hz, 7-H), 6.58 (d, J=12.0 Hz, 6-H).

1α-Hydroxy-secosterol 9a (X$^1$=X$^2$=H).

An ether solution (10 ml) of the 3β-acetate 9a as obtained in the preceding experiment was hydrolyzed using 10% sodium hydroxide in methanol at 23° C. under nitrogen for 0.5 h. The mixture was diluted with water (10 mL) and extracted with ether (3×50 mL). The combined ether extracts were washed with water (2×10 mL), saturated sodium chloride solution (2×10 mL), dried over anhydrous magnesium sulfate, filtered and evaporated to dryness under reduced pressure.

The residue was purified by HPLC on a Zorbax-Sil analytical column (4.6 mm×25 cm) using 5% isopropanol-hexane at 265 nm to give 9a (X$^1$=X$^2$=H).

High resolution mass spectral analysis: calc. for C$_{22}$H$_{34}$O$_2$, 330.2559; found 330.2541; UV (EtOH): λ$_{max}$ 264 nm λ$_{min}$ 227 nm; mass spectrum,: m/e (relative intensity) 330 (M$^+$, 55), 312(71), 287 (7), 269 (7), 251 (5), 189 (21), 152 (73), 134 (100); $^1$H-NMR (CDCl$_3$): δ0.54 (s, 18-H), 0.85 (d, J=7.0 Hz, 22-H), 0.93 (d, J=7.0 Hz, 21-H), 4.23 (m, 3-H), 4.42 (m, 1-H), 5.0 (s, 19(Z)-H), 5.34 (s, 19(E)-H), 6.02 (d, J=12.0 Hz, 7-H), 6.39 (d, J=12.0 Hz, 6-H).

5,6-trans-analog 10a (X$^1$=X$^2$=H)

The 3β-acetate (10a) was hydrolyzed in a similar manner and purified on HPLC using 5% isopropanol-hexane at 273 nm to give 10a (X$^1$=X$^2$=H). High resolution mass spectral analysis: calc. for C$_{22}$H$_{34}$O$_2$, 330.2559; found, 330.2532; UV (EtOH): λ$_{max}$ 273 nm, λ$_{min}$ 227 nm; mass spectrum: m/e (relative intensity), 330 (M$^+$, 69), 312 (48), 287 (21), 269 (18), 251 (15), 189 (31), 152 (76), 134 (100).

EXAMPLE 2

Preparation of Compounds 9b and 10b (X$^1$=X$^2$=H)

3β-Acetoxy-24-norchol-5-ene (2, R=ethyl)

A solution of 1 (R=Et) (0.5 g; Rf 0.8 in 25% ethyl acetate-hexane) in glacial acetic acid (7 mL) was heated at 70° C. for 4.5 h. The reaction mixture was cooled, poured into ice water, neutralized with 10% aqueous sodium hydroxide and extracted with chloroform (3×70 mL). The organic extract was washed with water (2×25 mL) and saturated sodium chloride (2×25 mL) and then dried over anhydrous magnesium sulfate. It was filtered and concentrated to dryness under reduced pressure to give 0.5 g of residue containing 2 (R=Et) (Rf 0.18 in 25% ethyl acetate-hexane) in ca. 90% yield. This material was used without further purification.

Mass spectrum: m/e (relative intensity) 372 (M$^+$, 1), 312 (100), 298 (38), 283 (7), 255 (12), 191 (30); $^1$H-NMR (CDCl$_3$): δ0.69 (s, 18-H), 0.82 (t, J=7.5 Hz, 23-H), 0.9 (d, J=7.0 Hz, 21-H), 1.05 (s, 19-H), 2.04 (s, 3-OCOCH$_3$), 4.58 (m, 3-H), 5.38 (d, J=4 Hz, 6-H).

3β-Acetoxy-24-norchola-5,7-diene (3) (R=Et)

A stirred solution of 2 (R=Et) (270 mg, 0.72 mmol) in dry hexane (50 mL) containing finely divided sodium bicarbonate (600 mg, 7.14 mmol) was heated to 80° C. at reflux under nitrogen and 1,3-dibromo-5,5-dimethylhydantoin (125 mg, 0.43 mmol) was then added. The reaction was allowed to proceed for 20 min at 80° C., then cooled and filtered. The filtrate was evaporated to dryness in vacuo. The residue was immediately dissolved in dry xylene (5 mL) and added dropwise to a mixture of xylene (30 mL) and s-collidine (174 mg, 1.44 mmol). The mixture was then flushed with nitrogen and refluxed at 145° C. for 1.5 h. It was then cooled, diluted with benzene (100 mL), washed with 3% aqueous hydrochloric acid (3×20 mL), saturated aqueous sodium bicarbonate (1×20 mL), saturated sodium chloride solution (2×20 mL), dried over anhydrous magnesium sulfate, filtered and evaporated to dryness under reduced pressure.

The residue was dissolved in dioxane (20 mL) and p-toluenesulfonic acid (60 mg, 0.32 mmol) was added. The mixture was flushed with nitrogen and refluxed at 70° C. for 30 min, cooled, diluted with water (10 mL) and then extracted with ethyl acetate (1×100 mL, 2×50 mL). The organic phase was washed with saturated aqueous sodium bicarbonate (1×25 mL), water (1×25 mL), saturated aqueous sodium chloride (2×30 mL) and then dried over anhydrous magnesium sulfate. It was filtered and evaporated under reduced pressure to dryness. The residue was chromatographed on preparative TLC using 10% ethyl acetate-hexane to yield 148 mg (54%) of 3 (R=Et). UV (EtOH): λ$_{max}$ 282 nm, 293, 272, 262, mass spectrum: m/e (relative intensity) 370 (M$^+$, 4), 328 (3), 310 (100), 296 (22), 253 (14), 158 (45), H-NMR (CDCl$_3$): δ0.63 (s, 18-H), 0.84 (t, J=7.5 Hz, 23-H), 0.95 (d, J=7.0 Hz, 21-H), 0.96 (s, 19-H), 2.04 (s, 3-OCOCH$_3$), 4.71 (m, 3-H), 5.4 (m, 7-H), 5.58 (m, 6-H).

3β-Hydroxy-24-norchola-5,7-diene (4) (R=Et)

Sodium hydroxide in methanol (10% solution) was added dropwise to a stirred solution of 3 (130 mg, 0.35 mmol, Rf 0.4 in 15% ethyl acetate-hexane) in ether (20 mL) under nitrogen. The reaction was allowed to proceed at 23° C. for 40 min. It was then diluted with ether (100 mL), water (20 mL) was added and the phases were separated. The aqueous layer was further extracted with ether (2×60 mL) and the ether extracts were combined, washed with water (2×30 mL), saturated aqueous sodium chloride (2×30 mL), dried over anhydrous magnesium sulfate, filtered and evaporated to dryness under reduced pressure. The residue was chromatographed on preparative TLC in 30% ethyl acetate-hexane to yield 103 mg (89%) of 4 (R=Et) (Rf 0.09 in 15% ethyl acetate-hexane).

UV (EtOH): λ$_{max}$ 282, 293, 272, 262 nm; mass spectrum: m/e (relative intensity), 328 (M$^+$, 100), 314 (16), 310 (8), 295 (86), 281 (15), 269 (45), 255 (13), $^1$H-NMR (CDCl$_3$): δ0.63 (s, 18-H), 0.84 (t, J=7.5 Hz, 23-H), 0.94

(d, J=7.0 Hz, 21-H), 0.96 (s, 19-H), 3.64 (m, 3-H), 5.38 (m, 7-H), 5.57 (m, 6-H).

Secosterol analog 5 (R=Et)

The 5,7-diene 4 (R=Et) (125 mg) in 1:4 dry benzene-ether (150 mL) was irradiated in a manner similar to that described in Example 1, above, for 25 min. The solvent was evaporated under reduced pressure. The crude residue was immediately dissolved in dry ethanol (30 mL) saturated with nitrogen. The solution was refluxed at 70° C. under nitrogen for 3 h, then cooled and concentrated under reduced pressure. Purification by preparative TLC using silica gel plates in 30% ethyl acetate-hexane afforded 5 (R=Et) (30 mg) in ca. 24% yield.

UV (EtOH): $\lambda_{max}$ 264 nm, $\lambda_{min}$ 227 nm; mass spectrum: m/e (relative intensity) 328 (M+, 23), 310 (3), 295 (10), 271 (9), 253 (11), 136 (81), 118 (100); $^1$H-NMR (CDCl$_3$): $\delta$0.55 (s, 18-H), 0.83 (t, J=7.5 Hz, 23-H), 0.92 (d, J=7.0 Hz, 21-H), 3.93 (broad, 3-H), 4.81 (m (sharp), 19(Z)-H), 5.01 (m (sharp), 19(E)-H), 6.02 (d, J=12.5 Hz, 7-H), 6.22 (d, J=12.5 Hz, 6-H).

Tosylate 6 (R=Et)

A solution of 5 (R=Et) (15 mg, 0.045 mmol; Rf 0.23 in 25% ethyl acetate-hexane) in dry pyridine (1 mL) was treated with p-toluenesulfonyl-chloride (20 mg, 0.105 mmol) at 5° C. under nitrogen for 24 h. The reaction was quenched with ice water and the mixture extracted with ether (3×50 mL). The organic phases were combined and washed with water (2×20 mL), 3% aqueous hydrochloric acid (2×20 mL), saturated sodium bicarbonate solution (2×20 mL) and saturated sodium chloride solution (1×20 mL), then dried over anhydrous magnesium sulfate and concentrated under reduced pressure to yield 22 mg of the tosylate 6 (R=Et) in greater than 95% purity.

Mass spectrum: m/e (relative intensity) 484 (M+, 8), 310 (72), 296 (18), 295 (20), 281 (10), 253 (39) 158 (65), 143 (47), 118 (100).

3,5-Cyclo-derivative 7 (R=Et)

The tosylate 6 (R=Et) (22 mg, 0.045 mmol; Rf 0.54 in 25% ethyl acetate-hexane) was added to a stirred suspension of finely divided sodium bicarbonate (60 mg, 0.71 mmol) in anhydrous methanol (20 mL). The mixture was heated at 55° C. under nitrogen for 8 h, cooled, diluted with ether (150 mL) and washed with water (2×30 mL) and saturated aqueous sodium chloride (2×30 mL). It was dried over anhydrous magnesium sulfate, filtered and concentrated under reduced pressure to yield a crude product 7 (R=Et) (Rf 0.6 in 25% ethyl acetate-hexane) in ca. 68% yield.

Mass spectrum: m/e (relative intensity) 342 (M+, 10), 328 (12), 310 (11), 295 (10), 253 (8), 149 (41), 136 (67), 118 (100).

1α-Hydroxy-3,5-cyclo-derivative 8 (R=Et)

t-Butyl hydroperoxide (14.0 μl, 0.1 mmol) was added to a suspension of selenium dioxide (2.4 mg, 0.022 mmol) in dry 1% pyridine-methylene chloride (10 mL) and cooled on an ice bath. The cyclovitamin 7 (R=Et) (15 mg, 0.044 mmol; Rf 0.6 in 25% ethyl acetate-hexane) in dry methylene chloride (5 mL) was added. The reaction was monitored on TLC and proceeded for 40 min before 10% sodium hydroxide (10 mL) was added to quench the reaction. The mixture was diluted with ether (150 mL), phases were separated and the ether phase was washed with 10% sodium hydroxide solution (2×30 mL), water (2×30 mL), sodium chloride (2×30 mL) and dried over anhydrous magnesium sulfate. It was then filtered and concentrated under reduced pressure. Preparative TLC using 25% ethyl acetate-hexane gave 8 (R=Et) (8 mg, Rf 0.18 in 25% ethyl acetate-hexane) in ca. 50% yield.

Mass spectrum: m/e (relative intensity) 358 (M+, 21), 326 (48), 285 (35), 269 (15), 191 (50), 135 (100); $^1$H-NMR (CDCl$_3$): $\delta$0.55 (s, 18-H), 0.85 (t, J=7.5 Hz, 23-H), 0.92 (d, J=7.0 Hz, 21-H), 3.27 (s, 6R-OCH$_3$), 4.18 (d, J=10 Hz, 6-H), 4.22 (m, 1-H), 4.95 (d, J=10 Hz, 7-H), 5.16 (d, J=2.0 Hz, 19(Z)-H), 5.26 (d, J=2.2 Hz, 19(E)-H).

5,6-cis and trans secosterol 3β-acetates 9b and 10b (X$^1$=Ac, X$^2$=H)

A solution of 8 (R=Et) (8 mg) in glacial acetic acid (0.5 mL) was heated to 55° C. under nitrogen for 15 min, cooled and poured over ice-cold sodium bicarbonate solution (15 mL). The mixture was extracted with ether (3×30 mL), and the ether extract was washed with saturated sodium bicarbonate solution (1×20 mL), water (2×20 mL), saturated aqueous sodium chloride (1×20 mL), dried over anhydrous magnesium sulfate and filtered. The filtrate was concentrated under reduced pressure and chromatographed by preparative TLC on 30% ethyl acetate-hexane (×2) to give the 5,6-cis-3β-acetate 9b (X$^1$=Ac, X$^2$=H) (Rf 0.13 on 25% ethyl acetate-hexane) and the 5,6-trans-3β-acetate 10b (X$^1$=Ac, X$^2$=H) (Rf 0.11 on 25% ethyl acetate-hexane).

The products were further purified on HPLC on a Zorbax-Sil column (4.6 mm×25 cm) in 1% isopropanol-hexane to give the acetates of 9b and 10b in 28.9% and 10.4% yields, respectively (retention volumes of 39 mL and 46.5 mL)

3β-Acetate 9b (X$^1$=Ac, X$^2$=H)

UV (EtOH) $\lambda_{max}$ 264 nm, $\lambda_{min}$ 226 nm; mass spectrum: m/e (relative intensity) 386 (M+, 17), 326 (45), 308 (8), 269 (16), 203 (17), 134 (100), $^1$H-NMR (CDCl$_3$): $\delta$0.55 (s, 18-H), 0.84 (t, J=7.5 Hz, 23-H), 0.92 (d, J=7.0 Hz, 21-H), 2.04 (s, 3-OCOCH$_3$), 4.41 (m, 1-H), 5.02 (m (sharp), 19(Z)-H), 5.22 (m, 3-H), 5.35 (m (sharp), 19(E)-H) 6.03 (d, J=12.5 Hz, 7-H), 6.35 (d, J=12.5 Hz, 6-H).

3β-Acetate 10b (X$^1$=Ac, X$^2$=H)

UV (EtOH) $\lambda_{max}$ 273 nm, $\lambda_{min}$ 226 nm; mass spectrum: m/e (relative intensity): 386 (M+, 12), 326 (64), 312 (8), 297 (9), 279 (4), 269 (21), 203 (28), 134 (100); $^1$H-NMR (CDCl$_3$): $\delta$0.56 (s, 18-H), 0.85 (t, J=7.5 Hz, 23-H), 0.93 (d, J=7.0 Hz, 21-H), 2.30 (s, 3-OCOCH$_3$), 4.49 (m, 1-H), 5.0 (m (sharp), 19(Z)-H), 5.14 (m (sharp), 19 (E)-H), 5.26 (m, 3-H), 5.82 (d, J=12.5 Hz, 7-H), 6.58 (d, J=12.5 Hz, 6-H).

1α-Hydroxy-secosterols 9b and 10b (X$^1$=X$^2$=H)

The 3β-acetate 9b (X$^1$=Ac, X$^2$=H) (1.5 mg, Rf 0.31 in 20% ethyl acetate-hexane) was hydrolyzed using 10% sodium hydroxide in methanol (2 mL) at 23° C. under nitrogen for 0.5 h. The mixture was diluted with ether (50 mL) and water (5 mL) was added. The phases were separated and the aqueous layer was extracted with ether (2×30 mL). The ether extracts were combined, washed with water (2×10 mL), saturated sodium chloride solution (2×10 mL), dried over anhydrous magnesium sulfate, filtered and concentrated under reduced pressure to give 9b (X$^1$=X$^2$=H) (Rf 0.06 in 20% ethyl acetate-hexane).

Similarly, acetate 10b (X$^1$=Ac, X$^2$=H) (0.75 mg, Rf 0.26 in 40% ethyl acetate-hexane) was hydrolyzed to give 5,6-trans-isomer 10b (R=Et, X$^1$=X$^2$=H) (Rf 0.06 in 40% ethyl acetate-hexane).

Each of the products was chromatographed on preparative TLC in 60% ethyl acetate-hexane, followed by HPLC on a Zorbax-Sil analytical column (4.6 mm×25 cm) in 7% isopropanol-hexane and then reverse phase HPLC (RPHPLC) on a Zorbax-ODS analytical column (4.6 mm×25 cm) in 90% methanol-water.

Compound 9b (X$^1$=X$^2$=H)

UV (EtOH): $\lambda_{max}$ 264 nm, $\lambda_{min}$ 227 nm; high resolution mass analysis: calc. for C$_{23}$H$_{36}$O$_2$, 344.2715; found, 344.2707; mass spectrum: m/e (relative intensity) 344 (M$^+$, 23), 326 (12), 287 (7), 269 (6), 251 (5), 203 (9), 152 (7), 134 (100); $^1$H-NMR (CDCl$_3$): δ0.52 (s, 18-H), 0.82 (t, J=7.5 Hz, 23-H), 0.90 (d, J=7.0 Hz, 21-H), 4.29 (m, 3-H), 4.42 (m, 1-H), 4.99 (m (sharp), 19(Z)-H), 5.31 (m (sharp), 19(E)-H), 6.0 (d, J=12.5 Hz, 7-H), 6.37 (d, J=12.5 Hz, 6-H).

5,6-trans-compound 10b (X$^1$=X$^2$=H)

UV (EtOH): $\lambda_{max}$ 273 nm, $\lambda_{min}$ 226 nm; high resolution mass analysis: calc. for C$_{23}$H$_{36}$O$_2$, 344.2715; found, 344.2705; mass spectrum: m/e (relative intensity) 344 (M$^+$, 12), 326 (6), 287 (4), 269 (4), 251 (3), 203 (6), 152 (30), 134 (100); $^1$H-NMR (CDCl$_3$): δ0.56 (s, 18-H), 0.84 (t, J=7.5 Hz, 23-H), 0.91 (d, J=7.0 Hz, 21-H), 4.22 (m (sharp), 3-H), 4.48 (m (sharp), 1-H), 4.96 (s, 19(Z)-H), 5.12 (m (sharp), 19(E)-H), 5.88 (d, J=12.5 Hz, 7-H), 6.57 (d, J=12.5 Hz, 6-H).

EXAMPLE 3

Preparation of compounds 9c and 10c

From 6β-methoxy-3α,5-cyclo-5α-cholane (compound 1, where R=propyl), processed through all the reaction steps given in Example 2 above under analogous experimental conditions, there is obtained the 1α-hydroxy-secosterol analog of structure 9c (X$^1$=X$^2$=H) and the corresponding 5,6-trans-compound of structure 10c (X$^1$=X$^2$=H).

EXAMPLE 4

Synthesis of Starting Material, Compound 1 (R=Me)

(a) (22E)-6β-Methoxy-3α,5-cyclo-5α-stigmast-22-ene (Stigmasterl i-methylether)

Freshly crystallized p-toluenesulfonyl chloride (20 g, 0.10 mole) was added to a solution of stigmasterol (25 g, 0.06 mole; Rf 0.26 in 30% ethyl acetate-hexane) in dry pyridine (250 mL). The reaction mixture was stirred at 23° C. for 24 h, after which it was slowly poured into saturated aqueous sodium bicarbonate solution. The precipitate was collected by filtration, washed with water several times until neutral and dried under reduced pressure overnight to yield stigmasteryl-3β-tosylate (32.06 g) in 93.2% yield.

The tosylate was converted to the i-ether without further purification. A solution of the tosylate (32 g, 0.06 mole) in chloroform (100 mL) was added slowly to a refluxed solution of finely divided sodium bicarbonate (30 g, 0.36 mole) in methanol (400 mL). The mixture was stirred at reflux for 14 h, cooled and concentrated to ca. 100 mL. Hexane was added (300 mL) and the resulting mixture was washed with water (100 mL). The phases were separated and the aqueous layer was back extracted with hexane (2×200 mL, 1×100 mL). The organic layers were combined and washed with water (2×100 mL), saturated aqueous sodium chloride (2×100 mL), dried over anhydrous magnesium sulfate, filtered and concentrated under reduced pressure to give 24 g of a crude oil containing the desired i-methyl ether (Rf. 0.52 in 10% ethyl acetate-hexane).

Mass spectrum: m/e (relative intensity) 426 (M$^+$, 87), 411 (34), 394 (54), 371 (59), 368 (19), 351 (21), 255 (61), 83 (100).

(b) 6β-Methoxy-3α,5-cyclo-23,24-dinor-5α-cholan-22-ol.

A stirred solution of stigmasteryl i-ether as obtained above (5.0 g, 11.7 mmol, Rf 0.64 in 30% ethyl acetate-hexane) in 1% pyridine-methylene chloride (100 mL) was cooled to −69° C. on a dry ice-acetone bath and treated with ozone generated by a Welsbach model T816 ozonator, until a pale blue color persisted due to excess ozone. The mixture was purged with oxygen for 5 min and allowed to warm to 23° C. Sodium borohydride (0.7 g, 18.4 mmol) in ethanol was added. After 2 h, the reaction mixture was diluted with ether (200 mL). Water (100 mL) was added, the phases were separated and the aqueous layer was extracted with ether (2×200 mL). The combined organic fractions were washed with saturated aqueous sodium chloride (2×50 mL) and dried over anhydrous magnesium sulfate, filtered and evaporated to dryness under reduced pressure. The residue was applied on a silica gel column and eluted using 20% ethyl acetate-hexane to afford 2.6 g of the desired 22-alcohol derivative in 65% yield. Mass spectrum: m/e (relative intensity) 346 (M$^+$, 75), 331 (52), 314 (89), 291 (100), 288 (30); $^1$H-NMR (CDCl$_3$): δ0.44 (m, 3-H), 0.65 (m, 4-H), 0.75 (s, 18-H), 1.04 (s, 19-H), 1.08 (d, J=7.0 Hz, 21-H), 2.77 (m, sharp, 6-H), 3.32 (s, 6-OCH$_3$).

(c) 6β-Methoxy-3α,5-cyclo-23,24-dinor-5α-cholan-22-yl tosylate p-Toluenesulfonyl chloride (2.0 g, 11 mmol) was added to a solution of the 22-alcohol obtained in the previous experiment (1.9 g; 5.5 mmol) in dry pyridine (35 mL). The reaction mixture was stirred at 23° C. for 18 h, then poured into ice-cold saturated aqueous sodium bicarbonate (50 mL) and extracted with ethyl acetate (2×150 mL, 1×100 mL). The organic extract was washed with water (3×50 mL), saturated sodium chloride (2×50 mL) and dried over anhydrous magnesium sulfate. It was then filtered and evaporated to dryness under reduced pressure. The residue was dried under reduced pressure overnight to give 2.2 g of the 22-tosylate in 91.0% yield. Mass spectrum: m/e (relative intensity) 500 (M$^+$, 69), 485 (49), 468 (100), 445 (79), 442 (20), 296 (20), 273 (24).

(d) 6β-Methoxy-3α,5-cyclo-23,24-dinor-5α-cholane (compound 1, R=Me)

To the 22-tosylate (2.15 g, 4 mmol) in anhydrous ether (100 mL) was added 0.22 g lithium alumnium hydride (liAlH, 0.22 g, 6 mmol). The reaction mixture was refluxed 10 h, cooled and excess reagent was decomposed by saturated aqueous sodium chloride. The mixture was filtered and the layers separated. The aqueous fraction was back-extracted with ether (2×100 mL). Ether fractions were combined, washed with water (1×50 mL), saturated sodium chloride solution (2×50 mL), dried over anhydrous magnesium sulfate, evaporated to dryness and dried under vacuum to give compound 1 (R=Me) in 96.0% yield. Mass spectrum: m/e (relative intensity) 330 (M+, 41), 315 (46), 298 (100), 283 (21), 275 (81), 272 (18), 177 (45); $^1$H-NMR (CDCl$_3$): δ0.40 (m, 3-H), 0.64 (m, 4-H), 0.72 (s, 18-H), 0.85 (d, J=7.0 Hz, 22-H), 0.92 (d, J=7.0 Hz, 21-H), 2.77 (m, sharp, 6-H), 3.35 (s, 6-OCH$_3$).

EXAMPLE 5

Preparation of Starting Material, Compound 1 (R=Et)

(a)

6β-Methoxy-3α,5-cyclo-24-nor-5α-cholane-23-nitrile.

To the 22-tosylate obtained in Example 4(c) above (10 g, 20 mmol, Rf 0.53 in 25% ethyl acetate-hexane) dissolved in dimethylsulfoxide (200 mL) was added sodium cyanide (1.95 g, 40 mmol). The mixture was stirred at 80° C. under nitrogen for 2 h, then cooled and stirred at room temperature for 1 h. It was then poured over ice-saturated ammonium chloride solution (250 mL) and extracted with ether (3×450 mL). The combined ether fractions were washed with water (3×200 mL), saturated sodium chloride (2×200 mL), dried over anhydrous magnesium sulfate, filtered and concentrated under reduced pressure to give the desired 23-nitrile derivative (7.05 g crude, Rf 0.57 in 25% ethyl acetate-hexane). The crude mixture was used in the next step without further purification. Mass spectrum: m/e (relative intensity) 355 (M+, 33), 340 (46), 323 (64), 308 (4), 297 (17), 300 (100), 218 (11), 149 (31); $^1$H-NMR (CDCl$_3$): δ0.43 (m, 3-H), 0.65 (m, 4-H), 0.74 (s, 18-H), 1.02 (s, 19-H), 1.15 (d, J=7.0 Hz, 21-H), 2.77 (t, J=2.5 Hz, 6-H).

(b) 6β-Methoxy-3α,5-cyclo-24-nor-5α-cholan-23-ol.

To the nitrile derivative as obtained in (a) above (7.0 g, 19.7 mmol, Rf 0.27 in 10% ethyl acetate-hexane) dissolved in dry benzene (150 mL) and cooled on ice under nitrogen was added slowly diisobutylaluminum hydride [DIBAL-H, 1.5 mole solution in toluene (20 mL, 30 mmol)]. The ice bath was removed after addition was complete and the reaction was allowed to proceed at 23° C. for 3 h. Methanol (150 mL) was added to decompose the aluminum salt complex and the mixture was poured over ice water (200 mL). The mixture was filtered and the aqueous layer was extracted with ether (3×150 mL). The organic phases were combined, washed with saturated sodium chloride (2×60 mL), dried over anhydrous magnesium sulfate and concentrated under reduced pressure to give 6.25 g of product. This product was a mixture of the original 23-nitrile and the expected 23-aldehyde. This mixture was again treated with the same reducing agent. Thus, the crude product was dissolved in dry benzene and treated with DIBAL-H (17.5 mL, 26.25 mmol). Work-up as before and chromatography of the residue on silica gel, eluted with 10% ethyl acetate-hexane yielded 0.85 g of the desired 23-alcohol derivative (Rf 0.03 in 10% ethyl acetate-hexane). Mass spectrum: m/e (relative intensity) 360 (M+, 75), 345 (59), 328 (99), 305 (100), 302 (29), 281 (22), 255 (23); $^1$H-NMR (CDCl$_3$): δ0.44 (m, 3-H), 0.65 (m, 4-H), 0.72 (s, 18-H), 0.93 (d, J=7.0 Hz, 21-H), 1.02 (s, 19-H), 2.77 (m, sharp, 6-H), 3.3 (s, 6-OCH$_3$).

The remainder of the product (2 g) was the corresponding 23-aldehyde, which, if desired, can be further reduced using the above conditions to yield additional quantities of the 23-alcohol product.

(c)

23-Hydroxy-6β-methoxy-3α,5-cyclo-24-nor-5α-cholane 23-tosylate.

p-Toluenesulfonyl chloride (0.95 g, 5.0 mmol) was added to a solution of the 23-alcohol obtained in (b) above (0.85 g, 2.36 mmol) in dry pyridine (10 mL). The reaction mixture was kept at 0° C. for 20 h, then poured into ice-cold saturated aqueous sodium bicarbonate (25 mL), extracted with ethyl acetate (3×100 mL), washed with water (3×40 mL), saturated sodium chloride (2×40 mL), dried over anhydrous magnesium sulfate, filtered and evaporated to dryness under reduced pressure to give the 23-tosylate (1.15 g) in ca. 95% yield. Mass spectrum: m/e (relative intensity) 514 (M+, 42), 499 (26), 482 (100), 468 (14), 459 (42), 456 (12), 361 (13), 255 (29).

(d) 6β-Methoxy-3,5-cyclo-24-nor-5α-cholane (compound 1, R=Et).

To the above tosylate (1.15 g, 2.08 mmol, Rf 0.7 in 10% ethyl acetate-hexane) in anhydrous ether (100 mL) was added LiAlH$_4$ (0.12 g, 3 mmol). The reaction mixture was refluxed 5 h, cooled and excess reagent was decomposed by saturated sodium chloride solution. The mixture was filtered, the phases were separated and the aqueous fraction was extracted with ether (2×100 mL). The ether extracts were combined, washed with water (1×50 mL), saturated sodium chloride (2×50 mL), dried over anhydrous magnesium sulfate, evaporated to dryness under reduced pressure and then dried under vacuum to give the desired 24-nor-cholane derivative (compound 1, R=Et) (0.59 g, Rf 0.64 in 10% ethyl acetate-hexane) in ca. 82% yield. Mass spectrum: m/e (relative intensity) 344 (M+, 9), 329 (12), 312 (19), 289 (22), 286 (4), 255 (7), 191 (11), 69 (90); $^1$H-NMR (CDCl$_3$): δ0.44 (m, 3-H), 0.65 (m, 4-H), 0.72 (s, 18-H), 0.82 (t, J=7.5 Hz, 23-H), 0.9 (d, J=7.0 Hz, 21-H), 1.02 (s, 19-H), 2.77 (m, sharp, 6-H), 3.32 (s, 6-OCH$_3$).

EXAMPLE 6

Preparation of Starting Material, Compound 1 (R=propyl)

Treatment of the 23-tosylate obtained in Example 5(c) above, with sodium cyanide under conditions analogous to those described in Example 5(a), provides 6β-methoxy-3α,5-cyclo-5α-cholan-24-nitrile. By reduction of this nitrile, using the procedure of Example 5(b) above, there is obtained 6β-methoxy-3α,5-cyclo-5α-cholan-24-ol. This alcohol is converted to the corresponding 24-tosylate derivative by a procedure analogous to that described in Example 5(c) above, and the 24-tosylate, subjected to hydride reduction as described in Example 5(d) above, then provides the desired compound, 6β-methoxy-3α,5-cyclo-5α-cholane (compound 1, where R=propyl).

Process Scheme I
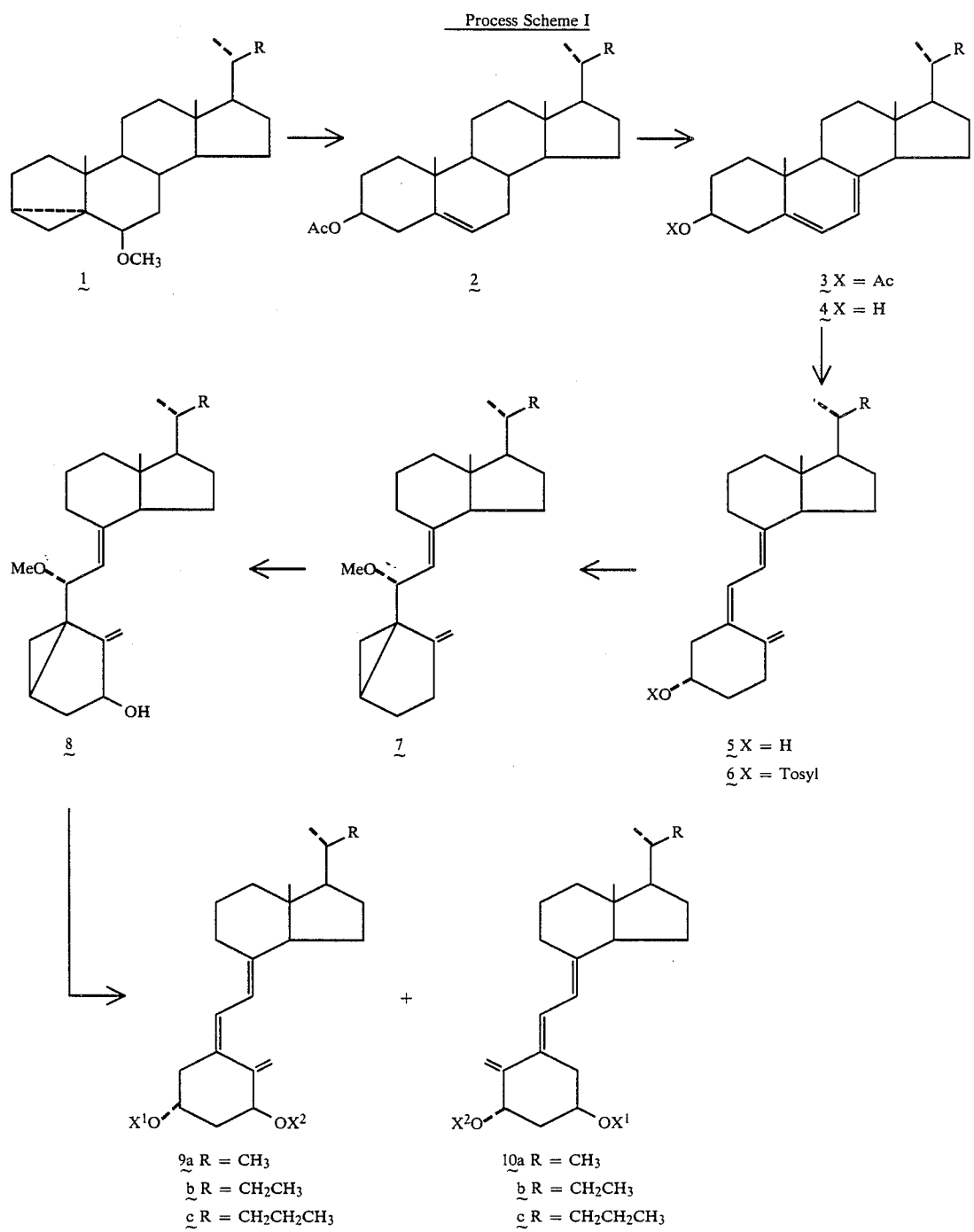
We claim:
1. A compound selected from the group consisting of

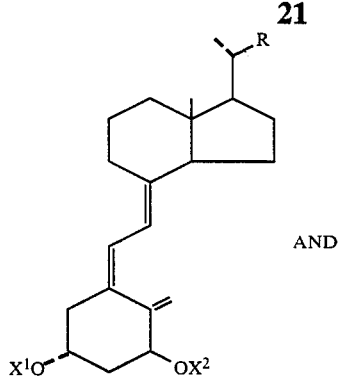

AND

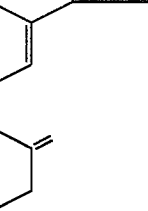

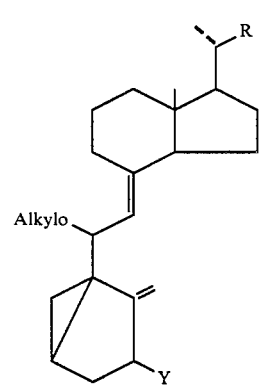

wherein R is selected from the group consisting of methyl, ethyl and propyl and wherein $X^1$ and $X^2$ represent, independently, hydrogen or an acyl group.

2. A compound as claimed in claim 1 wherein R is methyl and $X^1$ and $X^2$ represent hydrogen.

3. A compound as claimed in claim 1 wherein R is ethyl and $X^1$ and $X^2$ represent hydrogen.

4. A compound as claimed in claim 1 wherein R is propyl and $X^1$ and $X^2$ represent hydrogen.

5. A compound represented by the formula wherein R is selected from the group consisting of methyl, ethyl and propyl and wherein X is hydrogen or acyl.

6. A compound represented by the formula wherein R is methyl, ethyl or propyl.

7. A compound represented by the formula wherein R is methyl, ethyl or propyl.

8. A compound represented by the formula wherein R is methyl, ethyl or propyl and where Y is hydrogen or hydroxy.

9. A pharmaceutical composition comprising a compound represented by the structure:

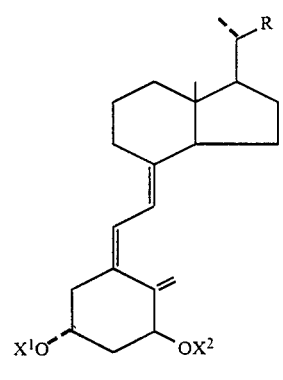

where R is selected from the group consisting of methyl, ethyl and propyl, and where $X^1$ and $X^2$ represent, independently, hydrogen or acyl, together with a pharmaceutically acceptable excipient.

10. A pharmaceutical composition according to claim 9 comprising a compound wherein R is methyl.

11. A pharmaceutical composition according to claim 9 comprising a compound wherein R is ethyl.

12. A pharmaceutical composition according to claim 9 comprising a compound wherein R is propyl.

* * * * *